United States Patent
Gegner et al.

(10) Patent No.: US 10,505,910 B2
(45) Date of Patent: Dec. 10, 2019

(54) PATIENT MONITOR AND METHOD FOR MONITORING A PATIENT

(71) Applicant: KONINKLIJKE PHILIPS N.V., Eindhoven (NL)

(72) Inventors: Guenter Gegner, Tuebingen (DE); Sebastian Hebler, Herrenberg (DE); Harald Greiner, Nufringen (DE); Jürgen Fischbach, Bandorf (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 566 days.

(21) Appl. No.: 15/038,238

(22) PCT Filed: Nov. 14, 2014

(86) PCT No.: PCT/EP2014/074647
§ 371 (c)(1),
(2) Date: May 20, 2016

(87) PCT Pub. No.: WO2015/078710
PCT Pub. Date: Jun. 4, 2015

(65) Prior Publication Data
US 2016/0292375 A1 Oct. 6, 2016

(30) Foreign Application Priority Data

Nov. 27, 2013 (EP) .................................. 13194590

(51) Int. Cl.
*G16H 10/60* (2018.01)
*H04L 29/06* (2006.01)
(Continued)

(52) U.S. Cl.
CPC .......... *H04L 63/08* (2013.01); *G06F 19/3418* (2013.01); *G16H 10/60* (2018.01);
(Continued)

(58) Field of Classification Search
CPC ....................................................... G16H 10/60
See application file for complete search history.

(56) References Cited

U.S. PATENT DOCUMENTS

| 5,331,549 A | 7/1994 | Crawford |
| 6,600,421 B2 * | 7/2003 | Freeman .............. A61B 5/7475 340/3.31 |

(Continued)

FOREIGN PATENT DOCUMENTS

| CA | 2595830 | 2/2009 |
| JP | 10323332 | 12/1998 |

(Continued)

*Primary Examiner* — John A Pauls (57) ABSTRACT

A patient monitor for monitoring a patient includes a sensor interface (106), a communication interface (108), a user interface (114), and a patient identification unit (115) for identifying the patient to be monitored. A processor (120) processes obtained sensor signals, received information and/or user input to obtain patient-related data, and a controller (121) controls said communication interface (108) to retrieve patient context information including information related to the patient, once the patient has been identified by the patient identification unit (115), available in a central administration system (102) from said central administration system (102) and/or other patient monitors (100b-100n) and controls said processor (120) to take received patient context information into account in the processing to obtain patient-related data.

12 Claims, 3 Drawing Sheets

(51) Int. Cl.
  *G06F 19/00* (2018.01)
  *G16H 80/00* (2018.01)
  *G16H 40/63* (2018.01)
  *G16H 50/30* (2018.01)
  *G16H 15/00* (2018.01)
(52) U.S. Cl.
  CPC ............ *G16H 40/63* (2018.01); *G16H 80/00* (2018.01); *G16H 15/00* (2018.01); *G16H 50/30* (2018.01)

(56) References Cited

U.S. PATENT DOCUMENTS

| | | |
|---|---|---|
| 8,038,593 B2 | 10/2011 | Friedman |
| 8,447,626 B2 | 5/2013 | Sun |
| 9,138,144 B2 | 9/2015 | Geva |
| 9,514,277 B2 | 12/2016 | Hassing |
| 2002/0046346 A1 | 4/2002 | Evans |
| 2003/0025604 A1 | 2/2003 | Freeman |
| 2006/0047538 A1 | 3/2006 | Condurso |
| 2008/0263625 A1 | 10/2008 | Gomez |
| 2009/0231124 A1* | 9/2009 | Klabunde ............ A61B 5/0205 340/539.12 |
| 2011/0145894 A1 | 6/2011 | Garcia |

FOREIGN PATENT DOCUMENTS

| | | |
|---|---|---|
| WO | 2006/051464 | 5/2006 |
| WO | 2012/117316 | 9/2012 |

* cited by examiner

PATIENT MONITOR AND METHOD FOR MONITORING A PATIENT

CROSS REFERENCE TO RELATED APPLICATIONS

This application is the U.S. National Phase application under 35 U.S.C. § 371 of International Application No. PCT/EP2014/074647, filed Nov. 14, 2014, published as WO 2015/078710 on Jun. 4, 2015, which claims the benefit of European Patent Application Number 13194590.9 filed Nov. 27, 2013. These applications are hereby incorporated by reference herein.

FIELD OF THE INVENTION

The present invention relates to a patient monitor and a corresponding method for monitoring a patient.

BACKGROUND OF THE INVENTION

Clinical care is based on information sharing across multiple care roles, including physician, nurse, patient, family, etc., to coordinate care. In many settings today, there is an overload of care information that may not be known to all members of the team, may not be relevant at a given decision point, or is relevant and is not known to the decision member at the time of decision.

Further, the care team is generally mobile and not physically looking at data represented in a central administration system for the patient of interest, such as EMRs (Electronic Medical Records) stored in a central server of a hospital, at the decision time. This creates an environment where errors are made due to incomplete knowledge of existing data, and workflow is impeded as the user needs to "drill" into the vast EMR to get the data, and timely collaboration with the rest of the care team delays good decision making and timely and correct care plan.

Patient monitoring devices (herein also called patient monitors) are contributing to this workflow today as measurement devices of vital signs and providing alarming and scoring based on the captured vital signs. In case a caregiver decides to visit a patient, vital signs, alarms and scores are available for review.

U.S. Pat. No. 6,600,421 discloses a system to automatically locally control a device according to preferences of a user entering a local area of the device from a remote area. The system provides a sensor generating measurement information based upon a patient parameter measured by the sensor and a processor managing local output of the measurement information according to automatically detected control signals locally and wirelessly transmitted from a transmitter entering a local area of the sensor from a remote area. The control signals include identification of a user and the transmitter travels with the user entering the local area of the sensor from a remote area so that the processor can manage local output of the measurement information according to stored preferences of the user. The processor can also control patient parameter measurements according to the preferences of the user.

WO 2006/051464 A1 (US 2009/0231124A1) discloses a wireless patient point-of-care network including a plurality of medical devices each with a wireless communication interface. Each medical device is configured to provide at least one medical service to a patient. A patient identification device is associated with the patient. The patient identification device includes a wireless communication interface in communication with the wireless communication interfaces of the medical devices. The patient identification device performs a patient identification service that wirelessly associates the medical devices with the patient.

SUMMARY OF THE INVENTION

It is an object of the present invention to provide a patient monitor and a corresponding method for monitoring a patient with improved functionalities that particularly improve and ease the work of caregivers at the point of care.

In a first aspect of the present invention a patient monitor is presented comprising:
  a sensor interface for receiving sensor signals obtained by one or more sensors for measuring a patient parameter,
  a communication interface for transmitting information to and receiving information from a central administration system and/or other patient monitors via a network,
  a user interface for reception of user input and for output of received sensor signals, information received from said central administration system and/or other patient monitors and/or of patient-related data derived from said sensor signals, received information and/or user input,
  a patient identification unit for identifying the patient to be monitored,
  a processor for processing said sensor signals, received information and/or user input to obtain patient-related data,
  a controller for controlling said communication interface to retrieve patient context information including information related to the patient, once the patient has been identified by the patient identification unit, available in said central administration system from said central administration system and/or other patient monitors and for controlling said processor to take received patient context information into account in the processing to obtain patient-related data.

In a further aspect of the present invention a corresponding method is presented comprising:
  identifying the patient to be monitored
  retrieving patient context information including information related to the patient, once the patient has been identified, available in a central administration system and/or other patient monitors from said central administration system and/or other patient monitors via a network,
  receiving sensor signals obtained by one or more sensors for measuring a patient parameter,
  processing said sensor signals, received information and/or user input to obtain patient-related data, taking received patient context information into account in said processing,
  outputting received sensor signals, information received from said central administration system and/or other patient monitors and/or patient-related data derived from said sensor signals, received information and/or user input, and
  transmitting received sensor signals, obtained patient-related data and/or user input to said central administration system via said network.

In yet further aspects of the present invention, there are provided a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed methods, processor, computer program and medium have similar and/or identical preferred embodiments as the claimed system and as defined in the dependent claims.

The proposed patient monitor and the proposed method represent a new class of device and method, respectively, allowing for vital signs taking, alarming, scoring and having access to complete patient context (e.g. EMR data) at the point of care (POC) of the patient monitor. Access to the complete patient context of patient data is e.g. granted by a caregiver management based on configurable point of care permissions to make sure a certain caregiver is allowed to do a dedicated set on actions on the patient monitor to increase patient safety. Information and patient context on the point of care patient monitor is presented to the caregiver and accessible to the caregiver based on the configurable point of care permissions.

In case a caregiver is triggered by information to go to see the patient, the patient monitors connected to the patient already has or can access on demand the full patient context, while allowing for data access and validation based on individual configured caregiver skills, expressed by point of care permissions. These permissions are independent from the permissions; a caregiver may have in a centralized or mobile working environment.

Thus, the present invention provides a unique device and method using context aware algorithms for presenting clinical information, allowing access to clinical information and communications controls, to facilitate workflow optimization and increase patient safety. The proposed patient monitor can be used in any environment including hospital, home, and during patient transport in between.

According to a preferred embodiment said controller is configured to control said communication interface to retrieve substantially the complete patient context information from said central administration system and/or other patient monitors immediately after the patient has been identified by the patient identification unit and/or to synchronize the patient monitor with the central administration system. In this way, all the relevant data that are available for a patient, including data that have been obtained at other patient monitors, are immediately available at the patient monitor at which the patient is currently identified so that all this information is immediately available for the caregiver.

In another embodiment said controller is configured to control said communication interface to transmit obtained sensor signals, patient-related data and/or user input to said central administration system and/or to synchronize the central administration system with the patient monitor. This provides that the central administration system is updated so that other patient monitors which may be used later for the same patient, e.g. at a different point of care within a hospital, are able to immediately obtain the complete updated patient context.

Preferably, said controller is configured to control said communication interface to transmit obtained sensor signals, patient-related data and/or user input to said central administration system after it has been obtained or updated or after confirmation by the user. Thus, the update of the central administration system can be made immediately and automatically or, alternatively, on request of the user, e.g. if certain measurements or calculations (e.g. of the patient's health score) have been confirmed by an authorized caregiver.

Advantageously, said patient identification unit is configured to automatically identify the patient when the patient monitor approaches the patient or the patient's local area and/or to identify the patient based on user input including information related to the identity of the patient. Thus, in one embodiment the patient can be easily identified, e.g. through use of an RFID chip carried by the patient and a corresponding RFID reader integrated into the patient monitor or by use of Bluetooth or Zigbee technology. Alternatively, the user may input the patient's identity when the patient monitor is first used for the particular patient.

In another embodiment the patient monitor further comprises a user identification unit for identifying the user of the patient monitor, wherein said controller is configured to is configured to control said communication interface to retrieve user context information including information related to the user, once the user has been identified by the patient identification unit, available in said central administration system and/or other patient monitors from said central administration system and/or said other patient monitors, to control said user interface to output received user context and to control said processor to take received user context information into account in the processing to obtain patient-related data. The identification of the user, e.g. a caregiver like a nurse or a physician, can be made automatically using the same or similar technology as explained above for identification of the patient, or the user may identify himself through a corresponding input.

Preferably, said user context information comprises user rights information for use by the controller to control the output of received sensor signals, information received from said central administration system and/or other patient monitors and/or of patient-related data by the user interface, to control the retrieval of information from the central administration system by the communication interface and/or to control the processing of sensor signals, received information and/or user input to obtain patient-related data by the processing unit.

Said user context information preferably comprises user preferences for use by the controller to control the output of received sensor signals, information received from said central administration system and/or other patient monitors and/or of patient-related data by the user interface and/or to control the receiving of sensor signals by one or more sensors. This makes it easier for a user to operate and use the patient monitor and to get the desired information in a desired format. Thus, valuable time of the user is saved.

Said patient context information may further comprise one or more of vital signs, vital signs histories, alarms, alarm histories, scores, notifications, notification histories, advisories, advisory histories, orders, order histories, work items, work item histories, status reports, patient attribute changes, protocols, protocol selection information, vital trends, alarm, sensor data requests, control data for controlling devices assigned to the patient, administration attributes selected scoring schemes, scoring protocol state.

In another embodiment said processor is configured to perform individual processing algorithms, in particular configurable scoring algorithms and/or auto-scheduled algorithms, to said sensor signals, received information and/or user input to obtain patient-related data. Thus, the patient monitor may act as a kind of autonomous device having a least some of the functions of the central administration system or of a conventionally used device/method to calculate patient-related data such as an early warning score. The patient monitor can generate new additional information by combining information e.g. by configurable scoring algorithms and auto scheduled algorithms.

In another embodiment said processor is configured to synchronize and update its patient-related data after receipt of patient context information. Thus, the patient monitor is always aware of the actual patient context.

in still another embodiment said processor is configured to process said sensor signals, received information and/or user input to obtain patient-related data irrespective if the patient monitor is connected to said central administration system or not. Thus, also in the non-connected state the patient monitor can act autonomously and process the desired patient-related data, which are only later (once the patient monitor gets connected to the central administration system) transmitted to the central administration system. This further improves the work of the caregiver since no connection to the central administration system to have the full patient context and e.g. to process obtained sensor data and calculate an early warning score.

Further, in an embodiment said communication interface is configured to transmit patient-related data, which has been obtained while said patient monitor was not connected to said central administration system, to said central administration system once the patient monitor gets connected to said central administration system.

According to preferred embodiments, each patient monitor identified for a certain patient at a time, allowing for having assigned multiple of the said patient monitors at the same time, perform individual algorithms on the individual available data and available patient context retrieved from and synchronized with the central administration system. The central administration system can perform individual algorithms on the individual available data and available patient context retrieved from and synchronized with the connected patient monitors, independent for multiple patients being assigned to the central administration system. Together the patient monitors and the central administration system build a synchronized patient context aware patient monitoring system. By being an equal contributor to the patient context aware patient monitoring system the individual patient monitor is always aware of the latest updated baseline of the patient context and updates individual generated data always immediately in relation of the synchronized patient context, allowing other patient monitors to immediately synchronize on their own, taking advantage in each individual available algorithm in the different patient monitors.

Further, by being an equal contributor to the centralized distributed patient management system a patient monitor can leave and re-enter the distributed patient management system at any time and working independent while not being connected to the centralized distributed patient management system. In the moment of re-entering the centralized distributed patient management system as an equal contributor, data context received and enriched while being offline is immediately updated based on a synchronization mechanism, and the patient context enriched while being offline is immediately available to all contributors (i.e. other patient monitors and the central administration system), to allow updating the developed gaps, resulting in an distributed synchronized patient context as if the patient monitor would have been available to the distributed patient management system all the time.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
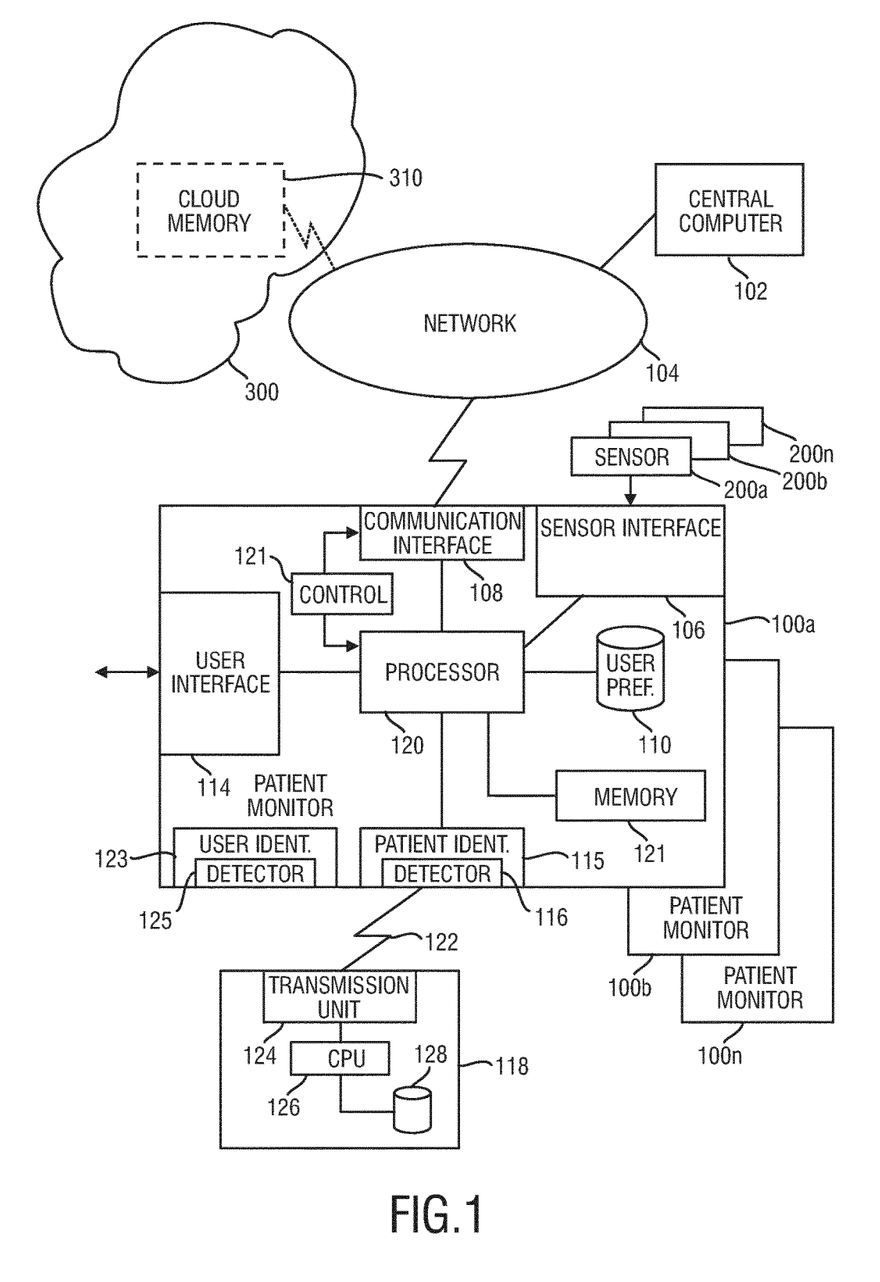
FIG. 1 shows a schematic diagram of an embodiment of a patient monitor according to the present invention.

FIG. 1 shows a schematic diagram of a distributed patient management system including an embodiment of a patient monitor according to the present invention. Apparatuses 100a-100n are patient monitors in communication with a central computer (a central administration system) 102 via network 104. The network 104 can be wired or wireless having a conventional topology and a conventional architecture. The architecture of network 104 can, for example, be client-server using conventional communication protocols. The network 104 can, for example, be a local area network or a wide area network, such as the Internet. The central computer 102 can be a conventional computer or computing device capable of storing, displaying and processing information, and communicating with patient monitors 100a-100n by receiving and transmitting information via the network 104 using conventional techniques.

The patient monitor 100a according to the present invention (which is explained in the following in more detail representative for all patient monitors 100a-100n) has a sensor interface 106 to receive sensor signals obtained by one or more sensors 200a-200n, such as transducers and other sensing devices, for measuring a patient parameter. Patient parameters can, for example, be cardiovascular parameters and temperature. The connection between the sensor interface 106 and the sensors 200a-200n may be established as a wireless (e.g. Bluetooth, Zigbee, WLAN) or a wired connection.

Further, a communication interface 108 (also called network interface) is provided for transmitting information to, receiving information from and synchronizing with a central administration system and/or other patient monitoring devices via a network. The communication interface 108 is provided for communicating, using conventional (wired or wireless) techniques, with the central computer 102 via the network 104.

A user interface 114 is provided for reception of user input and for output of received sensor signals, information received from said central administration system and/or other patient monitoring devices and/or of patient-related data derived from said sensor signals, received information and/or user input. The local (near sensors of the patient monitor, bed/patient-side, in-room) user interface 114 preferably provides interfaces with local output devices for local information output. The local output interface 114 can include, for example, a display unit visually presenting measurements (e.g., a graphical or wave presentation), a recorder presenting the measurements in a print format, and a sound unit/audio unit annunciating alarms or audibly providing the measurements, and an input/output unit for communication with other local equipment. Therefore, the patient monitor 100a can output the generated measurements to the local output interface for viewing, hearing and analysis by users (e.g., nurses and doctors). The user interface 114 may further include, for example, a keypad to provide manual command input for the patient monitor 100a.

A patient identification unit 115 is provided for identifying the patient to be monitored. In the embodiment shown in FIG. 1 the patient identification unit 115 includes a detector 116 that uses wireless technology 122 to automatically detect control/information signals locally transmitted from a transmitter 118 carried by the patient, when the transmitter comes within a predetermined distance from the detector 116. When the transmitter 118 enters a local area of the sensors patient monitor 100a from a remote area, e.g. when the patient monitor is brought to the patient for use as bedside monitor or when the patient approaches a patient monitor located at a different room, the detector 116 automatically detects wireless control signals transmitted by the transmitter 118. The local area can be defined, for example, as a room in which the patient is being monitored or a predetermined short distance, such as 20 feet radius, from sensor interface 106 (the bed-side patient monitor 100) according to system and application design specifications. The local area can also be defined according to or within applicable communication distance specifications of the particular wireless technology 122 used, such as 10 meters according to Bluetooth wireless technology specification. Preferably the detection system operates within a limited range so that signals transmitted from other transmitters 118, for example, outside of a room are detected infrequently. The detector 116 and transmitter 118 can use wireless technology 122 (detection system) such as infrared technology (e.g., IrDA standard) and radio technology. Radio technologies can include, for example, wireless networking (e.g., IEEE 802.11 B standard), local radio frequency (RF) (e.g., Bluetooth and HomeRF standards) and Ultra-Wideband Radio (UWB).

Still further, the patient monitor 100a comprises a processor 120 for processing said sensor signals, received information and/or user input to obtain patient-related data. In an embodiment said processor 120 is configured to execute software to generate the patient-related data from the measurements, e.g. by performing various processing functions, such as trending, archiving, reporting and diagnostics.

A controller 121 is provided for controlling the communication interface 108 to retrieve patient context information including information related to the patient, once the patient has been identified by the patient identification unit, available in said central administration system from said central administration and/or other patient monitoring devices 102b-102n. Further, the controller 121 controls the processor 120 to take received patient context information into account in the processing to obtain patient-related data.

Storage devices 110 (e.g. for storing user preferences) and 112 (for generally storing data) that store information, such as memory, hard drives, or drives for removable media (e.g., CD-R, CD-ROM, CD-RW, DVD-ROM and DVD-RAM) may be provided in or connected to the patient monitor 100a by conventional techniques to provide local storage for the patient monitor 100. Alternatively, a remote storage, such as a storage 310 in a network or in a cloud 300, may be used for this purpose.

The processor 120 is preferably in communication with and executes software to control not only the communication interface 108 and the processor 120, but also the storage devices 110 and 112, the user interface 114 and the detector patient identification unit 115, preferably using conventional techniques, so that the patient monitor 100a can automatically detect the presence of a patient in the immediate area of the patient monitor, typically a patient room. Alternatively, the patient assignment to the patient monitor can be performed in an automated way through the centralized administration system or through user interaction of a user through the user interface 114 of the patient monitor or of the central administration system.

The communication interface 108, user interface 114, storage devices 110 and 112, and patient identification unit 115 are preferably integrated within the patient monitor 100a, but may (some or all) be arranged locally external to the patient monitor 100a and in communication with patient monitor 100a using conventional techniques. The processor 120 and the controller 121 can be one or more processing units integrated with or external to patient monitor 100a. In case of being external, processor 120 and controller 121 would be local and in communication with patient monitor 100a using conventional interfaces and techniques. Software of an existing patient monitor can be modified to incorporate the processes of the present invention. Alternatively, a local external processing unit 120 and controller 121, which are in communication with the patient monitor and a local external patient identification unit 115, can execute software implementing the processes of the present invention, obviating modifying existing patient monitor software.

Preferably, detector 116 and transmitter 118 use wireless radio frequency technology because of radio frequency's better omni-directional communication capability than infrared's (IR) line-of-sight communication capability. For example, IR signals can be lost if the user traveling with the transmitter 118 turns his/her back to the detector 116, or the transmitter 118 is covered, for example, by clothing. Further, preferably detector 116 and transmitter 118 use wireless radio frequency that operates at the 2.4 GHz—the Industrial-Scientific-Medical (ISM) band. Further, preferably wireless technology 122 limits interference with other devices operating in the ISM band. Further, preferably detector 116 and transmitter 118 cause minimal, if any, electromagnetic interference with other electronic equipment/devices. Further, preferably wireless technology 122 supports automatic linking (i.e., establishing communication) when transmitter 118 comes into a specified distance range of detector 116.

In a preferred embodiment, detector 116 and transmitter 118 use the commercially available Bluetooth wireless technology because such technology is known to limit interference with other devises operating in the ISM band as well as cause minimal electromagnetic interference with other electronic devices. The Bluetooth wireless technology is low-power (1 milliwatt), short range (10 meters), can operate at the 2.4 GHz ISM band and supports automatic linking between mobile devices.

Transmitter 118 preferably includes a transmission unit 124 wirelessly transmitting information signals for automatic detection by detector 116. As discussed above, transmission unit 124 can use RF and IR wireless technology 122. In one embodiment, transmitter 118 can include a processor 126 executing software controlling transmitter 118 according to the present invention. Transmitter 118 can also include a storage unit 128. The storage unit 128 can be conventional memory storing user information, such as user identification information and user preferences. The transmitter 118 can use conventional techniques for power, such as a battery.

Preferably, a user identification unit 123 is provided for user identification, i.e. identification of the caregiver, such as a nurse or a clinician, who is going to use the patient monitor 100a. The user identification unit 123 may generally use the same technique as described above, i.e. detect a transmission unit carried by the user and may include a detector 125 that uses wireless technology to automatically detect control/ information signals locally transmitted from a transmitter (not shown, but similar or identical to the transmitter 118) carried by the user, when the transmitter comes within a predetermined distance from the detector 125. The patient monitor 100*a* can thus automatically detect the presence of a clinician, such as a nurse or a doctor, in the immediate area of the patient monitor, typically a patient room, and assume a "personality" consistent with the clinician's role. A patient monitor 100 can also assume an appropriate "personality" when no clinical staff is in the vicinity by providing customized default configurations. Alternatively, the user identification unit 123 may be configured to enable a user to manually enter his identity or insert an identification card, which techniques may also be used for patient identification instead of the above described technique.

Patient monitoring environments include, for example, centrally controlled bed-side patient monitors and stand-alone bed-side patient monitors. In a typical system environment the patient monitors are located in patient rooms. In case of the centrally controlled bed-side patient monitors, the patient monitors include a communication interface for communicating measurements and other information to the central administration system 102 represented by one or more central computers or servers. For example, a central computer 102 can be connected via a network (wire or wireless) to each patient monitor via the communication interface 108 of the patient monitor. The central computer 102 can, for example, be located at the nurse station in a hospital. A typical central computer 102 includes a local (computer-side, in-room) output interface.

A patient monitor is typically controlled as follows: personnel (e.g., nurses) at the nurse station can manually input commands at the central computer to control each patient monitor. Further, commands can be manually input via the local user interface of the patient monitor to control the patient monitor. Monitor control functions can include, for example, commands manually input to set and adjust monitoring and local measurement output configurations, and to control transmission of the measurements to the central computer via the communication interface of the monitors. For example, a patient monitor's local measurement output configuration can be set to sleep mode by turning off local output of sound and display.

Conventional patient monitors typically have only limited capabilities to process data and generate patient-related data such as an early warning score for the patient. Further, the complete patient-context, i.e. all information available for a particular patient, is generally not available at a particular patient monitor. This is different for the proposed and above described patient monitor 100*a* which is aware of the full patient context. Hereby, patient context awareness of the patient monitor generally means that vital signs, alarms, scores and further patient context derived from the patient monitoring device itself, other patient monitors, and the central administration system (including e.g. an EMR (Electronic Medical Record), lab and order systems, and centralized management systems), which all together form a distributed patient management system, are available to the patient monitor 100*a*.

The central administration system thus works as a distributed system that synchronizes patient context retrieved from external hospital administration systems and additional/updated patient context from patient monitors where the patient has been identified at before and in the moment. Further, the central administration system takes the inputs/updates from the various sources with the patient monitor being an equal contributing and consumer element.

The proposed patient monitor 100*a* further preferably provides user awareness meaning the role and permission based management of caregiver's point of care patient monitoring access rules. This allows configuring individual access to patient information at the point of care monitor allowing for user individual levels of data access, data validation, data presentation and assignment of caregivers to patients.

In the following an embodiment of a use model of the proposed patient monitor is intended to be enabled. On a hospital ward multiple patient monitors are available to be used for vital signs taking on patients. Various deployments are used today:

Pool Models (multi-patient workflow): the caregiver moves the patient monitor from patient to patient to take vital signs.

A patient monitor is provided at every bedside (single patient workflow): The patient is admitted to a certain bed, and therefore to a specific monitoring equipment; the patient may be transferred from one bed to another one, e.g. to acuity change, request for isolation, etc. at any point in time.

Today in both workflows (single patient/multiple patients) every patient monitor used has no context and no history of the patient and vital signs taking, and therefore begins with non-patient related defaults and no history. The caregiver has to review context within the patient record (manually/electronically), but the patient monitors do not have access to the current status/baseline of the patient.

With the patient monitor and method according to the present invention, regardless which patient monitor is used on a patient, the following improvements can be achieved:

i) Every patient monitor (immediately) synchronizes the full patient context, not only for review (prior art, electronic medical record), but for seamless monitoring, acknowledgment of (already existing and active) alarms and notifications, validation and reassessment of (already existing and active) data, continued monitoring on the current baseline (vital signs status, active alarms and notifications, EWS baseline, already validated data, . . . ) of this patient. This is achieved by fully modeled data, i.e. the patient monitor understands whatever data type will be synchronized and processes data of the patient as if they were generated locally. For the connected patient monitors this leads to a seamless electronic medical record of the patient as if they were connected all the time to one device, without artifacts within vital signs, alarms, notifications, pending order status, etc.

ii) The synchronized patient context includes ADT (Admission Discharge Transfer) patient attribute changes, CDS (Clinical Decision Support) protocol selection for the patient, e.g. EWS (Early Warning Scoring, Sepsis Screening, Triage Acuity State), vital signs and vital trends, active alarms and alarm history.

iii) Active notifications and notification history are provided and used, e.g. the latest EWS deterioration notifications, sepsis warnings, triage acuity change notifications, pending worklist items and history, e.g. pending vital signs or lab data requests, remote control of devices assigned to the same patient.

iv) Therefore, the workflow of the caregiver is simplified and patient safety is further enhanced. When exchanging a patient monitor, because of e.g. a more/less acuity device is needed the current patient status (patient baseline) is immediately available on the new patient monitor and the does not need to begin from zero. The patient monitor can immediately notify on the changes of the patient from data captured on the other patient monitor. As an example, this shall be illustrated for a score change notification: The score is 1 on patient monitor 1 and 2 on patient monitor 2. The score change from score 1 to score 2 is announced from patient monitor 2. The patient monitor 2 has taken over score from patient monitor 1 as baseline to announce the change of the patient. Without this enhancement the change of the score would have not been possible to be announced, because only new captured vital signs would have been available to analyze. Further, the score change can be visualized on patient monitor 1, patient monitor 2, by paging, and in the EMR, i.e. where ever the patient context is needed. The caregiver is able to review and acknowledge this score change notification on every patient monitor assigned to this patient (i.e. patient monitors 1 and 2). Thus, the full patient context is available to decide for acknowledging. Further, in a multi-patient workflow a caregiver admits a patient to the monitor and can now review the vital signs history and the pending recommendations/patient orders for that patient before taking the next steps and therefore based on the already existing status/baseline of the patient.

According to an aspect of the present invention the configuration of the individual permissions a caregiver (user) will have on the point of care patient monitor can be configured directly on the device or shared with a centralized system. Permissions can be assigned to individual caregivers or to roles summarizing a set of permissions. These roles can be assigned to the caregivers, containing the POC (Point of Care) permissions.

Figure 2:
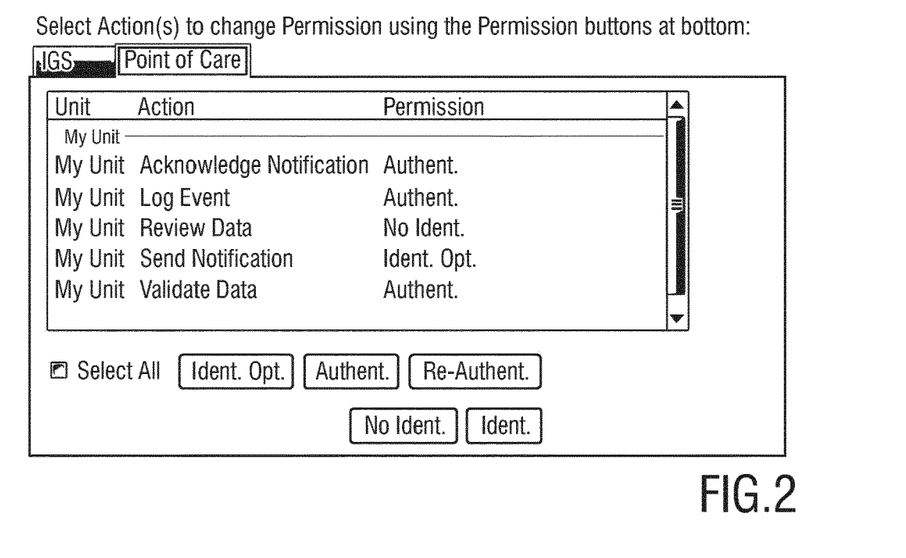
FIG. 2 shows an example of the configuration of the individual permissions of a caregiver.

FIG. 2 illustrates an example of the configuration of the individual permissions a caregiver (user) will have on the point of care patient monitor. This configuration can be configured directly on the patient monitor or shared with a centralized system, e.g. the central administration system. Permissions can be assigned to individual caregivers or to roles summarizing a set of permissions. These roles can be assigned to the caregivers, containing the POC permissions.

According to another aspect of the present invention POC (Point of Care) user identification and authentication is enabled, allowing for users to access patient information on the point of care monitors while working standalone or connected to a system.

According to another aspect of the present invention an execution engine (represented by the processor and/or controller) on the point of care patient monitor is provided analyzing individual user permissions and therefore granting/denying access to patient data and modifying data presentation. Examples are POC data validation, POC advisory acknowledge, etc. The user interface of these tasks on the patient monitor is only enabled in the patient monitor if the user has the appropriate permissions. As an example, after a caregiver is logged on, a patient is identified and a first MEWS (Modified Early Warning Score) is calculated, the data are checked for correctness and confirmed, e.g. by selecting a corresponding smart key ("store and validate") on the display of the patient monitor. The validated data is then sent to the central administration system. For this validation the user must have the POC data validation permission. As another example a spot check trend initiated by selecting another smart key shows the complete patient EWS history. For this the user must have the POC data review permission.

Figure 3:
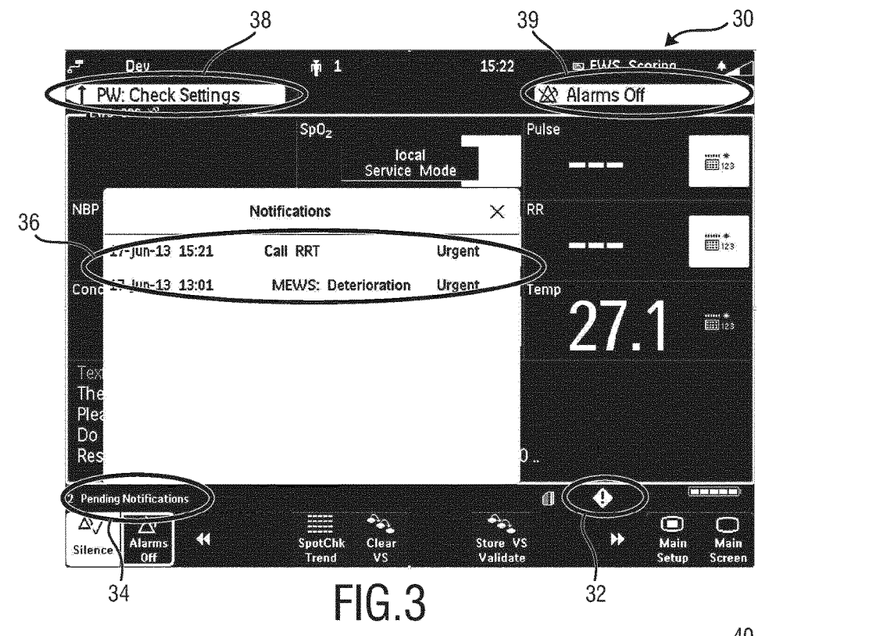
FIG. 3 shows an example of derived scoring notifications synchronized to a patient monitor.

As another example user acknowledgement may be enabled at a patient monitor as illustrated by the example of FIG. 3 showing a screen 30 of a patient monitor. The patient status of all notifications is synchronized back to patient monitor and available there for further caregiver action. The availability of notifications requiring caregiver interaction may be indicated visually on the display of the patient monitor, e.g. by a colored (e.g. red) exclamation mark 32. A prompt 34 may show the number of available notifications and a list 36 may show the notifications in detail. Further, the synchronized alarm status 38, 39 of the patient may be indicated. Each individual notification in the notification list can be operated and acknowledged by the caregiver. This clinically stops the paging of the notification. For this the caregiver needs to have the POC acknowledge notification permission to acknowledge. The acknowledgment dialog will ask the user for identification/authentication before acknowledgement (depending on configuration). Each task requiring user identification/authentication in addition to the given POC permission is logged with the given user identification.

Figure 4:
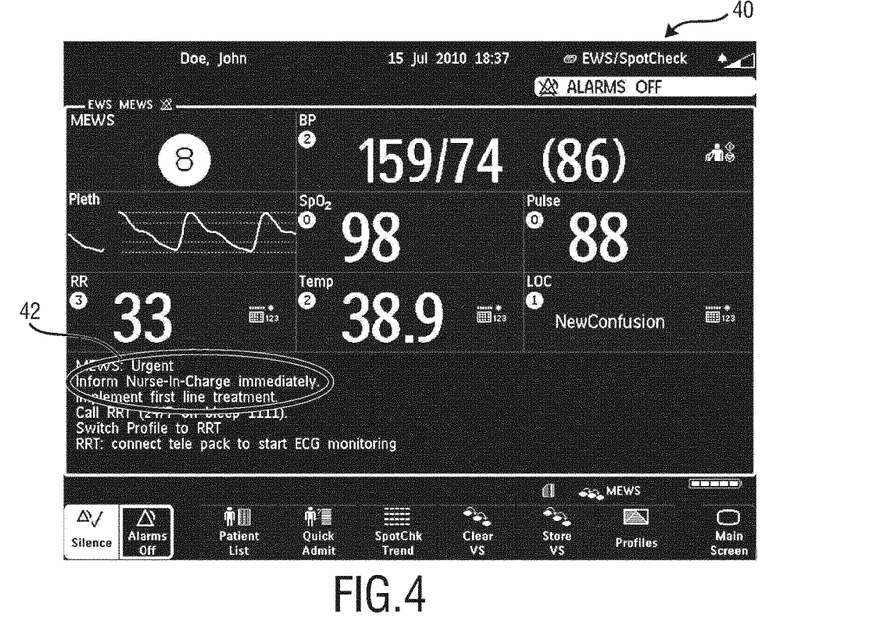
FIG. 4 shows an example of user awareness within recommendations derived from various states of a patient scoring protocol.

As still another example individual EWS recommendations may be provided at a patient monitor as illustrated by the example of FIG. 4 showing another screen 40 of a patient monitor. If a caregiver with e.g. the role and permissions of a 'Nurse-In-Charge' is logged in to the patient monitor, a recommendation 42 'Inform Nurse-In-Charge immediately' does not need to be issued. Having the knowledge of the permissions and roles of this caregiver the EWS could present a completely other set of recommendations to this caregiver.

According to another aspect of the present invention patient context awareness is provided to receive full patient context from various systems and other patient monitors to guarantee full patient context while measuring actual data on this or other devices connected and assigned to a patient. The patient status is synchronized to the patient monitor. Patient data locally stored or remote accessible and available for further processing is accessible on the patient monitor by the caregiver based on individual caregiver permissions.

Figure 5:
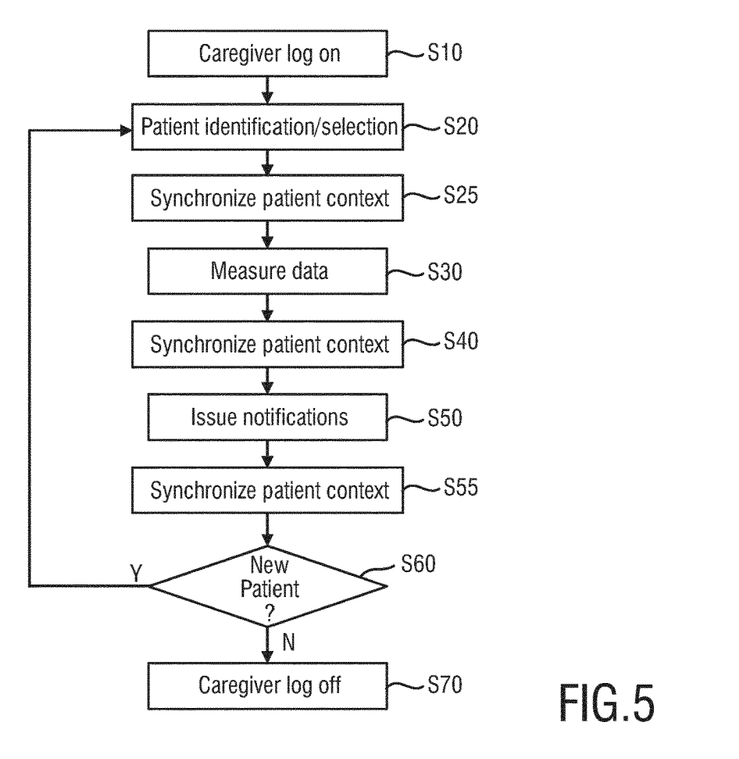
FIG. 5 shows a flowchart of an embodiment of a method according to the present invention.

FIG. 5 shows a flowchart of an embodiment of a method according to the present invention. In particular, the multi-patient workflow for a caregiver with patient context synchronization functionality available, embedded in a user awareness workflow, is illustrated.

In a first step S10 the caregiver logs on to the patient monitor as explained above, e.g. by entering his identity, scanning his badge (e.g. reading a barcode), automatic recognition of his identity, etc.

In a step S20, performed in parallel, before or after step S10, the patient is identified/selected, again by entering his identity, scanning his badge or wristband (e.g. reading a barcode), automatic recognition of his identity, etc. Preferably, only the account number is scanned, the other data of the patient (name, age, gender, date of birth, patient category, etc.) are all obtained automatically from the central administration system and are included in the dialog with the central administration system. After selecting confirm on the patient monitor, the patient is admitted. Then, an EWS protocol/patient context history already assigned to this patient is automatically synchronized for further review and validation. The EWS protocol decides which parameters have to be measured for that patient and which are the appropriate thresholds for announcing notifications.

In step S25 the patient context is optionally synchronized. The patient context generally includes one or more of (preferably all of) the vital signs, vital signs histories, alarms, alarm histories, scores, notifications, notification histories, advisories, advisory histories, orders, order histories, work items, work item histories, status reports, patient attribute changes, protocols, protocol selection information, vital trends, alarm, sensor data requests, control data for controlling devices assigned to the patient, administration attributes selected scoring schemes, scoring protocol state. The Sequence of reviewing history data and performing the next steps with the patient is generally completely free to the user. Each step and change will be (immediately) synchronized. Preferably, the data are checked for correctness and confirmed, e.g. by selecting a corresponding smart key on the display of the patient monitor. The validated data is sent to the central administration system. A spot check trend may illustrate the complete patient EWS history.

In step S30 the patient state is assessed by measuring data, such as heart beat, temperature, respiration rate, blood pressure, etc. and providing manual information, such as position at which pulse is taken, the patient posture, etc. From the available data patient-related data, such as the MEWS, is automatically calculated and output.

In step S40 the patient context is optionally synchronized again.

In step S50 active notifications regarding the particular patient synchronized to the currently used patient monitor are issued, which are ready for review and acknowledgment.

In step S55 the patient context is optionally synchronized again.

In step S60 the workflow continues with a new patient, i.e. returns to step S20, if desired.

In step S70 the user is logged off, either automatically after a certain time or actively by hitting a logoff smart key. Depending on user awareness configuration access to patient data (vital signs, notifications, alarm, etc.) can now be completely prohibited, without taking away the core functionality of a patient monitor to measure new data and alarm and notify on new data.

The present invention provides a unique methodology using context aware algorithms for presenting clinical information, audio, video and communications controls to facilitate workflow optimization and reduce alarm fatigue and information overload. The proposed device and method can be used in any environment including hospital, home, and during patient transport in between.

According to the present invention the patient monitor is not only a source of information, which is provided to the central administration system for further processing, but the patient monitor is source and sink of information and is thus an equal contributor to the distributed patient management system formed by the central administration system and the distributed patient monitor(s). The patient monitor thus transmits information, receives information, processes information and synchronizes with the central administration system to make sure that the complete up-to-date patient context is generally always available at a patient monitor that shall be used for a particular patient and at the central administration system. It is thus generally irrelevant which contributor of the distributed patient management system generates or processes any particular information. This makes it much easier and faster for a caregiver to perform his desired task right at the place of the patient.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A patient monitor for monitoring a patient comprising:
a sensor interface configured for receiving sensor signals obtained by one or more sensors for measuring a patient parameter,
a communication interface configured for transmitting information to and receiving patient context information from a central administration system and/or other patient monitors via a network,
a user interface configured for reception of user input and for output of:
received sensor signals,
information received from said central administration system and/or other patient monitors, and
patient-related data derived from said sensor signals, received information and/or the user input,
a patient identification unit configured for identifying the patient to be monitored, and
a controller configured for:
controlling said communication interface to retrieve and store the patient context information including information related to the patient, once the patient has been identified by the patient identification unit, available in said central administration system from said central administration system and the other patient monitors,
performing scoring algorithms and/or auto-scheduled algorithms, using said sensor signals when the patient monitor is out of communication with the central administration system and using the received patient context information stored by the controller,
synchronizing the patient monitor with the central administration system by controlling the communications interface to transmit the patient-related data, which has been obtained while said patient monitor was not connected to said central administration system, to said central administration system once the patient monitor becomes connected with the network, and,
wherein said patient context information comprises:
vital signs, vital signs histories, alarms, alarm histories, scores, notifications, notification histories, advisories, advisory histories, orders, order histories, work items, work item histories, status reports, patient attribute changes, protocols, protocol selection information, vital trends, alarms, sensor data requests, control data for controlling devices assigned to the patient, administration attributes selected scoring schemes, and a scoring protocol state which are stored in the central administration system.

2. The patient monitor as claimed in claim 1,
wherein said controller is configured to control said communication interface to retrieve the patient context information from said central administration system and other patient monitors immediately in response to the patient being identified by the patient identification unit.

3. The patient monitor as claimed in claim 1, wherein said controller is configured to control said communication interface to synchronize the central administration system with the patient monitor.

4. The patient monitor as claimed in claim 1, wherein said controller is configured to control said communication interface to transmit obtained sensor signals, patient-related data and user input to said central administration system after it has been obtained or updated and after confirmation by the user.

5. The patient monitor as claimed in claim 1, wherein said patient identification unit is configured to automatically identify the patient when the patient monitor approaches the patient or the patient's local area.

6. The patient monitor as claimed in claim 1, further comprising:
a user identification unit configured for identifying the user of the patient monitor, wherein said controller is configured to control said communication interface to retrieve user context information including information related to the user, once the user has been identified by the user identification unit, available in said central administration system and other patient monitors and control said user interface to output received user context.

7. The patient monitor as claimed in claim 6, wherein said user context information comprises user rights information for use by the controller to control the output of:
received sensor signals,
the patient context information received from said central administration system and other patient monitors, and
the patient-related data by way of the user interface, and
to control the retrieval of information from the central administration system by the communication interface.

8. The patient monitor as claimed in claim 6, wherein said user context information comprises user preferences for use by the controller to control the output format of:
the received sensor signals,
the patient context information received from said central administration system, and
patient-related data by way of the user interface.

9. The patient monitor as claimed in claim 6, wherein said user context information comprises:
user preferences for use by the controller to control the receiving of sensor signals by the one or more sensors.

10. A non-transitory computer-readable medium carrying program code configured to cause a computer or patient monitor to carry out the steps of a method comprising:
identifying the patient to be monitored;
with the patient monitor connected to a network, retrieving via the network patient context information including at least vital signs histories, alarms, alarm histories, scores, and vital trends related to the identified patient, from a central administration system and from other patient monitors and measuring patient data by sensors of the patient monitor;
with the patient monitor disconnected from the network, measuring the patient data and analyzing the measured patient data using the patient context information previously retrieved from the central administration system to generate alarms, notifications, establish base lines, validate data, conduct clinical decision support protocols, analyze patient acuity, determine trends, and create an alarm history;
upon establishing communication with the network, synchronizing patient data between the monitor and the central administration system to transfer patient data which has been measured by the patient monitor and any alarms, notifications, base lines, acuity analyses, trends and alarm history obtained by analyzing the measured patient data while the patient monitor was not connected to the network to the central administration system and to transfer any context information obtained by the central administration and/or other monitors while the patient monitor was disconnected from the network from the central administration system and/or other monitors to the patient monitor.

11. A method for monitoring a patient comprising:
identifying a patient to be monitored at a patient monitor;
while the patient monitor is connected with a network, retrieving patient context information pertaining to the identified patient from a central administration system via the network;
measuring patient data with sensors and reporting the sensor data to the patient monitor when the patient monitor is connected or disconnected from the network;
with the patient monitor disconnected from the network, analyzing the measured patient data using the patient context information previously retrieved from the central administration system to generate alarms, notifications, establish base lines, validate data, conduct clinical decision support protocols, analyze patient acuity, determine trends, and create an alarm history;
upon establishing communication with the network, synchronizing patient data between the monitor and the central administration system to transfer patient data which has been measured by the patient monitor and any alarms, notifications, base lines, acuity analyses, trends and alarm history obtained by analyzing the measure patient data while the monitor was not connected to the network to the central administration system and to transfer any context information obtained by the administration system and/or other monitors while the patient monitor was disconnected from the network from the central administration system and/or other monitors to the patient monitor.

12. A patient monitor for monitoring a patient comprising:
a sensor interface configured for receiving sensor signals obtained by one or more sensors for measuring a patient parameter;
a communication interface configured for transmitting information to and receiving patient context information from a central administration system and/or other patient monitors via a network;
a user interface configured for reception of user input and for output of:
received sensor signals,
information received from said central administration system and/or other patient monitors, and
patient-related data derived from said sensor signals, received information and/or the user input,
a patient identification unit configured for identifying the patient to be monitored; and
one or more processors configured to:

with the patient monitor disconnected from the network, analyzing the patient-related data derived from the sensor signals using the patient context information previously retrieved from the central administration system to generate alarms, notifications, establish base lines, validate data, conduct clinical decision support protocols, analyze patient acuity, determine trends, and create an alarm history, upon establishing communication with the network, synchronizing patient data between the monitor and the central administration system by controlling the communication interface to transfer patient-related data which was derived from sensor signals and any alarms, notifications, base lines, acuity analyses, trends and alarm history obtained by analyzing the measure patient data while the monitor was not connected to the network to the central administration system and to transfer any context information obtained by the administration system and/or other monitors while the patient monitor was disconnected from the network from the central administration system and/or other monitors to the patient monitor.

\* \* \* \* \*